United States Patent [19]

Chiba et al.

[11] Patent Number: 5,190,764
[45] Date of Patent: Mar. 2, 1993

[54] AGENT FOR IMPARTING A SUSTAINED RELEASE PROPERTY TO A PESTICIDE, A PESTICIDE HAVING A SUSTAINED RELEASE PROPERTY AND A PROCESS FOR THE PRODUCTION THEREOF

[75] Inventors: Kaoru Chiba, Fujisawa; Shinji Yonemura; Tatsuo Noguchi, both of Atsugi; Takuo Wada, Hatano; Satoru Moriyama, Atsugi, all of Japan

[73] Assignee: Hokko Chemical Industry Co., Ltd., Tokyo, Japan

[21] Appl. No.: 920,525

[22] PCT Filed: Mar. 3, 1989

[86] PCT No.: PCT/JP89/00231
§ 371 Date: Nov. 3, 1989
§ 102(e) Date: Nov. 3, 1989

[87] PCT Pub. No.: WO89/07889
PCT Pub. Date: Sep. 8, 1989

Related U.S. Application Data

[63] Continuation of Ser. No. 439,352, Nov. 3, 1989, abandoned.

[30] Foreign Application Priority Data

Mar. 3, 1988 [JP] Japan .................................. 63-48635

[51] Int. Cl.$^5$ ............................................ A01N 25/34
[52] U.S. Cl. .................................. 424/408; 424/419; 424/417; 424/420; 424/497
[58] Field of Search ............... 424/420, 497, 419, 408, 424/487; 514/86, 122, 469, 143; 71/92, 121, 87

[56] References Cited

U.S. PATENT DOCUMENTS

| | | | |
|---|---|---|---|
| 2,962,418 | 11/1960 | Sawyer | 424/420 |
| 3,497,345 | 2/1970 | Duyfies | 71/105 |
| 3,577,515 | 3/1971 | Vandegaer | 424/497 |
| 3,761,589 | 9/1973 | Balassa | 514/86 |
| 3,920,442 | 11/1975 | Albert | 71/92 |
| 4,065,555 | 12/1977 | Potter | 424/419 |
| 4,183,740 | 1/1980 | Jang | 71/92 |
| 4,511,395 | 4/1985 | Misselbrook | 71/121 |
| 4,698,264 | 10/1987 | Steinke | 424/408 |
| 4,732,762 | 3/1988 | Sjogren | 424/408 |
| 4,871,541 | 10/1989 | Shibanai | 424/408 |
| 4,936,901 | 6/1990 | Surgant | 71/87 |

FOREIGN PATENT DOCUMENTS

1167321 10/1969 United Kingdom.

Primary Examiner—Thurman K. Page
Assistant Examiner—William E. Benston
Attorney, Agent, or Firm—Larson & Taylor

[57] ABSTRACT

A sustained release pesticide comprises solid pesticidal particles comprising a solid, pesticidally active ingredient, substantially the whole surface of the pesticidal particles being coated with a hydrophobic substance.

20 Claims, No Drawings

AGENT FOR IMPARTING A SUSTAINED RELEASE PROPERTY TO A PESTICIDE, A PESTICIDE HAVING A SUSTAINED RELEASE PROPERTY AND A PROCESS FOR THE PRODUCTION THEREOF

This application is a continuation of application Ser. No. 07/439,352 filed Nov. 3, 1989, abandoned.

TECHNICAL FIELD

This invention relates to an agent for imparting a sustained release property to a pesticidally active ingredient having solid particulate form in a pesticide or a pesticide preparation containing the solid particles of the pesticidally active ingredient, and this invention also relates to a new pesticide having the sustained release property and containing the pesticidally active ingredient which has been treated with the agent for imparting the sustained release property thereto, and further this invention includes a process for the production of such solid particles of a pesticidally active ingredient which have gained a sustained release property. More particularly, this invention is directed to a technique for controlling the release of a pesticidally active ingredient from the pesticide by covering the particle surfaces of said pesticidally active ingredient of solid particulate form with fine particles or powder of a hydrophobic substance.

BACKGROUND ART

Hithereto, many efforts have been made to impart a sustained release property to various kinds of pesticidally active ingredients having solid form or liquid form. When largely classified, the prior art methods for preparing a pesticide having the sustained release property include (1) a method comprising encapsulating a pesticidal active ingredient in micro-capsules (see Japanese patent application first publication "Kokai" No. 58-144204 gazette and Japanese patent application first publication "Kokai" No. 59-20209 gazette); (2) a method comprising converting a pesticidally active ingredient into an inclusion compound with cyclodextrin (see Japanese patent application first publication "Kokai" No. 58-21602 gazette and Japanese patent application first publication "Kokai" No. 59-53401 gazette); (3) a method comprising granulating solid particles of a pesticidally active ingredient for use in a pesticide preparation such as granules and powders etc., alone or together with a filler etc., and coating the resultant particulate cores with wax or one of various resins (see Japanese patent application first publication "Kokai" No. 57-126402 gazette and Japanese patent application first publication "Kokai" No. 60-202801 gazette), and others. Hitherto, however, no attempt was made to achieve an improvement in the art by depositing and adhering fine particles of a hydrophobic substance onto the particle surfaces of a pesticidally active ingredient having a solid particulate form so as to cover the particle surfaces of the active ingredient with the fine particles of the hydrophobic substance, and thus controlling the dissolution and release of said pesticidally active ingredient.

When a pesticide preparation having a solid state in the form of granules and powders is brought into contact with water after the application of said pesticide preparation for use, in some cases the active ingredient present in said preparation can rapidly dissolve out and be released from the pesticide preparation so that the concentration of the active ingredient as released exceeds such a concentration just required for the active ingredient to display its biological effects. In these cases, the active ingredient can occasionally bring about kill of the leave of crop plants or a phytotoxicity such as suppression of the growth of crop plants; and the active ingredient once released can be degraded or disappear fastly in water or soil; and also it can disappear due to its degradation under the action of light, with consequences that the period of time of the lasting of the biological activities of the active ingredient can be shortened. For these reasons, these various troublesome problems can be solved if such a measure is provided to ensure that the pesticidally active ingredient continues to release gradually over a prolonged period of time from the pesticide preparation only in minimum amounts of the active ingredient just required to achieve the control of a pest. Further, when the sustained release property can be imparted to a pesticide, the necessity of repeated applications of such pesticide at several times can be eliminated, and the pesticide can be utilized highly economically with serving to prevent the enviromental pollution. However, any of the known pesticides having the sustained release property as mentioned above are advantageous in some aspects but disadvantageous in another aspects in solving the aforesaid various troublesome problems.

Thus, certain pesticidal compounds cannot be encapsulated into micro-capsules or cannot be converted into the inclusion compound with cyclodextrin according to the nature of the pesticidal compounds, and for these reasons there exist such pesticidal compounds which cannot be processed into a pesticide preparation having the sustained release property. Even if the prior art methods for producing the pesticide preparations having the sustained release property are applicable, there often occur some cases where a satisfactory sustained release property cannot be obtained; where the pest-controlling activities of the resulting pesticide preparation are not displayed fully; and/or where lasting and prolongation of the biological activities as well as the reduction in the phytotoxicity of the active compound which are aimed at for one of the purposes of the pesticide having the sustained release property are not attainable to a full extent. Besides, for the reasons why the technique for production of a pesticide having the sustained release property is complicate and troublesome and the raw materials used therefor are expensive; and for another reasons, there are still remaining many problems that are to be solved in the technical aspect or in the economic aspect. As described in the above, therefore, the prior art technique for the production of a pesticide having the sustained release property has not yet been developed to a full extent, and a development of a novel technique therefor is now desired.

In account of the above situations, we, the present inventors, have paid attention on a technique of modifying or improving the structure of the surfaces of particles of such a pesticidally active ingredient having solid particulate form, and we have made researches in attempts to provide a novel agent which is able to give the desired sustained release property to a pesticide of the solid particulate form, and to provide such a pesticide having the sustained release property as obtained using said agent, and also to provide a process for the production of such sustained-releasing pesticide.

DISCLOSURE OF THE INVENTION

We, the present inventors, have made eargerly studies in order to solve the above-mentioned technical problems. As a result, we have found that an appropriate sustained release property can be imparted to the particles of the pesticidally active ingredient by modifying the surfaces of the particles of the pesticidal active ingredient having the solid particulate form so that the particle surfaces of the active ingredient become exhibiting a higher hydrophobic property than the original property inherently shown by the particle surfaces of the active ingredient. When this is explained more concretely, it has now been found by us that when the whole surfaces of the particles of a pesticidally active ingredient having solid particulate form are coated evenly either with such an outer layer consisting or composed of fine particles of a hydrophobic substance which have a particle diameter of not greater than one-fifth of the average or mean particle diameter of said pesticidally- active ingredient and have been adhered or fixed onto the aforesaid surfaces of the particles of the pesticidally active ingredient, or with such a continuous or cohesive coat-film which has been formed by integrating and binding the above-mentioned adhered or fixed individual particles of the fine particles of the hydrophobic substance with each other, it is possible to produce such composite particles of the pesticidally active ingredient that are each containing a solid particle of the pesticidally active ingredient as a central core within each composite particle and also are each provided with a surrounding outer layer consisting of the fine particles of the hydrophobic substance or consisting of a coating film as made of the integrated and bound particles of said hydrophobic substance. At this time, it has further been found that where the total amount of the fine particles of the hydrohobic substance employed is adjusted to be of such a proportion that the hydrophobic substance is present in an amount ranging from 0.05 parts to 1 part by weight for 1 part by weight of the pesticidally active ingredient, and when the above-mentioned composite particles are placed in water, the pesticidally active ingredient is able to dissolve out gradually from the core portion of said composite particles through the surrounding outer layer made of the hydrophobic substance, and thus the resulting composite particles of the pesticidally active ingredient can exhibit the sustained release property for the pesticidal active ingredient.

Furthermore, it has now been found that the composite particles of the pesticidal active ingredient which are produced as described in the above may be, similarly to the conventional pesticides, formulated into such forms as powders, granules, wettable powders, suspensions, pastes and the like, by mixing with auxiliary additives and fillers, and that the pesticide formulations so made can exhibit an appropriate sustained-releasing effect on the active ingredient and hence exhibit the biological activity inherent to the pesticidal active ingredient in a lasting way and over a prolonged period of time, with consequences that some merits such as a remarkable reduction in the phytotoxicity of the active ingredient are obtained.

In a first aspect of this invention, therefore, there is provided an agent for imparting a sustained release property to a pesticide containing solid particles of a pesticidally active ingredient, characterized in that said agent comprises or is fine particles of a hydrophobic substance.

In a second aspect of this invention, there is also provided a pesticide having a sustained release property, characterized in that either said pesticide contains such composite particles containing a pesticidally active ingredient and each comprising a central core of the pesticidally active ingredient and an outer layer consisting of fine particles of a hydrophobic substance surrounding said core, which composite particles are produced by adhering to and over the particle surfaces of solid particles of the pesticidally active ingredient fine particles of the hydrophobic substance having an average or mean particle diameter of not greater than one-fifth of the average or mean particle diameter of solid particles of said pesticidally active ingredient or by partially embedding and thus fixing individual particles of the fine particles of the hydrophobic substance into the particle surfaces of the particles of the pesticidally active ingredient; or said pesticide contains such composite particles containing the pesticidally active ingredient and each comprising a central core of said pesticidally active ingredient and a continuous or cohesive coat-film made of the hydrophobic substance surrounding said core, which composite particles are produced by adhering said fine particles of the hydrophobic substance to and over the particle surfaces of solid particles of the pesticidally active ingredient or partially embedding and thus fixing individual particles of the fine particles of the hydrophobic substance into the particle surfaces of said pesticidaly active ingredient and then integrating and binding the so adhered or fixed individual particles of the fine particles of the hydrophobic substance with each other by application of impacting force and/or heat of friction to make the integrated and bound particles of the hydrophobic substance to coat the surfaces of the core particles of the pesticidally active ingredient, and that the total amount of the fine particles of the hydrophobic substance used is of a proportion in the range of 0.05 parts to 1 part by weight of the hydrophobic substance per 1 part by weight of the pesticidally active ingredient.

In a third aspect of this invention, this invention include a process for the production of a pesticide in the form of composite particles each comprising a central core of a pesticidally active ingredient and either an outer layer consisting of fine particles of a hydrophobic substance surrounding said core or a continuous or cohesive coat-film made of the hydrophobic substance, characterized in that the process comprises using fine particles of the hydrophobic substance having an average or mean particle diameter of not greater than one-fifth of the average or mean particle diameter of solid particles of the pesticidally active ingredient in such a proportion that the total amount of the hydrophobic substance employed is in a range of 0.05 parts to 1 part by weight per 1 part by weight of said pesticidally active ingredient, and adhering fine particles of the hydrophobic substance to and over the particle surfaces of solid particles of the pesticidally active ingredient or alternatively partially embedding and thus fixing individual particles of the fine particles of the hydrophobic substance into the particle surfaces of said pesticidally active ingredient, and further, if desired or if appropriate, integrating and binding the so adhered or fixed individual particles of the fine particles of the hydrophobic substance with each other by application of impacting force and/or heat of friction to make the integrated and bound particles of the hydrophobic substance to coat wholly the surfaces of the core particles of the pesticidally active ingredient.

BEST MODE FOR WORKING THE INVENTION

The hydrophobic substance which constitutes the fine particles of the hydrophobic substance usuable in this invention is not limited specifically, if it is a substance having a water-repellent property to water. Where one drop of water is fallen onto a top horizontal surface of a plane plate which has been made by shaping the fine particles of a hydrophobic substance under compression, and if the hydrophobic substance then used is hydrophobic to the required extent, the fallen water drop does then neither wet the surface of said plane plate nor spread over the plate surface, with retaining the shape of one single drop of water. At this time, as the "angle of contact" of said hydrophobic substance is defined such an angle which is formed between the surface of the solid plate and the liquid surface of water drop at the place where the free surface of the stationary water drop is contacting with the surface of the plane plate. When this angle of contact is greater, it can be assumed that the hydrophobic property of the hydrophobic substance is higher.

In accordance with this invention, the "angle of contact" of a hydrophobic substance to water, which is taken as a criterion of the hydrophobic property of a hydrophobic substance, may be measured by the following method of measurement:

A disc in the form of a tablet of 8.5 mm in diameter which is made of a hydrophobic substance and weighing 100 mg is prepared by shaping fine particles of said hydrophobic substance into tablet under compression (200 kg/cm$^2$) in a tablet-shaping machine. On the top surface of this tablet is then placed by dropping through a micro-syringe 5 $\mu$l of water which has been deionized by ion-exchange resins. One minute after the dropping, the angle of contact formed between the water droplet and the tablet surface is measured by means of a goniometer (Type G-1, produced by Elma Optical Company).

Where a hydrophobic substance shows a hydrophobic property to such a degree that the angle of contact formed between the free surface of the water drop and the tablet surface of said hydrophobic substance is 70° C. or more when measured by the above-mentioned method of measurement, this hydrophobic substance may be very much effective to be used in this invention.

The hydrophobic substances usuable in this invention include the under-mentioned substances, for example, to which this invention is not limited, of course.

(1) Higher aliphatic acids

These acids include stearic acid, palmitic acid, lauric acid, myristic acid and the like, for example.

(2) Metal salts of higher aliphatic acids

These salts include aluminum stearate, magnesium stearate, calcium stearate and the like, for example.

(3) Titanium dioxide treated with metal salts of higher aliphatic acids

These treated titanium dioxides include titanium dioxide treated with aluminum laurate, titanium dioxide treated with aluminum stearate, and the like, for example.

(4) Hydrophobic white carbon, namely hydrophobilized silica

These materials include an alkylsilylate silica, especially silicon dioxide treated with dimethyldichlorosilane, and the like, for example.

(5) Hydrophobic synthetic polymers

These polymers include polystyrenes, polyamides, silicones and the like, for example.

For these hydrophobic substances, commercially available hydrophobic substances may be utilized as such. If necessary, however, commercially available hydrophobic substances may be finely ground before their use in order to ensure that the average or mean particle diameter of the hydrophobic substances is adjusted to be not greater than one-fifth of the average or mean particle diameter of a pesticidally active ingredient as employed.

The average particle diameter of a hydrophobic substance used in this invention may vary according to the average particle diameter of a pesticidally active ingredient as employed, but it is necessary that the hydrophobic substance has an average or mean particle diameter of not greater than one-fifth of the particle diameter of the pesticidally active ingredient. It is preferable that the hydrophobic substance has an average or mean particle diameter of not greater than one-tenth of the particle diameter of the active ingredient. Where the hydrophobic substance has an average particle diameter of greater than one-fifth of the particle diameter of the active ingredient, it becomes difficult to adhere or fix the fine particles of the hydrophobic substance uniformly into the particle surfaces of the pesticidally active ingredient or to apply the hydrophobic substance as a continuous or cohesive coat-film of a uniform thickness onto the particle surfaces of the active ingredient, so that the hydrophobic substance will then display incompletely its function to impart the sustained release property to the active ingredient.

Further, it is desirable that the composite particles of the pesticidally active ingredient which each comprise a core of said pesticidally active ingredient and an outer coating layer or sheath of the hydrophobic substance surrounding said core have an average or mean particle diameter of not more than 50 microns. If the composite particles have an average or mean particle diameter of more than 50 microns, it is involved that the pesticidally active ingredient does not display its desired biological activity to a full extent. As a tentative guideline, the average or mean particle diameter of the solid particles of the pesticidally active ingredient which form the core in the composite particles may be in a range of 5 microns to 500 microns but is not restricted to this particular range. However, the average particle diameter of the solid particles of the active ingredient may generally vary according to the nature of the active ingredient compound and according to the forms of the pesticide formulations. Again, the average or mean particle diameter of the hydrophobic substance may be in a range of 0.01 microns to 100 microns but is not restricted to this particular range.

Furthermore, the amount of the hydrophobic substance which is applied onto the surfaces of the solid particles of the pesticidally active ingredient may vary according to the average particle diameter of the pesticidally active ingredient and according to the average particle diameter of the fine particles of the hydrophobic substance, but it is necessary that the hydrophobic substance is applied to the particle surfaces of the active ingredient in such a proportion that the hydrophobic substance applied is in a range of 0.05 parts to 1 part by weight for one part by weight of the pesticidally active ingredient. Of course, it is admittable that the ratio of the amount of the hydrophobic substance to the amount of the pesticidally active ingredient may appropriately be changed within the above-mentioned range in order to obtain an optimal degree of the sustained-release property for the active ingredient. However, if the amount of the fine particles of the hydrophobic substance is less than 0.05 parts by weight, it will be not fully achievable to adhere or fix the fine particles of the hydrophobic substance uniformly to and over the whole surfaces of the particles of the pesticidally active ingredient, or to apply the hydrophobic substance as a uniform coat-film to the surfaces of the particles of the active ingredient, so that the effects of imparting the sustained release property will not be attainable completely. On the contrary, if the amount of the hydrophobic substance used is more than 1 part by weight so as to bring about an excessive application of the fine particles of the hydrophobic substance to and around the particles of the pesticidally active ingredient, the effects of imparting the sustained release property can be displayed but it is then invoked that the biological activity inherently possessed by the pesticidally active ingredient can be reduced. Accordingly, it is not desirable that the fine particles of the hydrophobic substance are used excessively over the amount just required for the intended purpose.

The pesticidally active ingredient having solid particulate form usuable in this invention is not restricted to a particular sort, and any sort of the pesticidally active ingredient may be usuable as long as it is an active ingredient compound which has been used for conventional pesticides or pesticidal preparations. Examples of such pesticidally active ingredient include the under-mentioned pesticidal compounds, for example, to which this invention is not limited, of course.

EXAMPLES OF INSECTCIDES

Pyridafenthion, chlorpyrifos-methyl, chlorpyrifos, vamidothion, dimethoate, phosalone, PMP, DMTP, CVMP, dimethylvinphos, acephate, salithion, DEP, EPN, NAC, MTMC, MIPC, BPMC, PHC, MPMC, XMC, ethiofencarb, pirimicarb, bendiocarb, resmethrin, rotenone, CPCBS, kelthane, chlorobenzilate, chloropropylate, phenisobromolate, tetradifon, quinomethionate, amitraz, benzomate, binapacryl, tricyclohexyltin hydroxide, namely cyhexatin, fenbutatin oxide, polynactin complex, methyl isothiocyanate, mesulfenfos, morantel tartrate, endosulfan, cartap, thiocyclam, methomyl, oxamyl, butoxycarboxim, diflubenzuron, buprofezin and the like.

EXAMPLES OF FUNGICIDES AND BACTERIOCIDES

Copper sulfate, basic copper sulfate, basic copper oxychloride, cupric hydroxide, copper oxinate, captan, zineb, maneb, maneozeb, polycarbamate, propineb, ziram, thiuram, milneb, captafol, dichlofluanid, TPN, fthalide, tolclofos-methyl, thiophanate-methyl, benomyl, thiabendazole, iprodione, vinclozolin, procymidone, blasticidin S, kasugamycin, polyoxins, validamycin A, streptomycin, oxytetracycline, nobobiocin, mildiomycin, PCNB, hydroxyisoxazole, dazomet, chloroneb, triphenyltin hydroxide, MAF, MAFA, dithianon, phenazine oxide, CNA, dimethirimol, anilazine, oxycarboxin, mepronil, probenazole, isoprothiolane, methasulfocarb, fluoroimide, triforine, triadimefon, tricyclazole, fosetyl, guazatine, metalaxyl and the like.

EXAMPLES OF HERBICIDES

MCP, MCPP, MCPB, phenothiol, naproanilide, DNBP, ioxynil, CNP, chlomethoxynil, bifenox, MCC, IPC, phenmedipham, MBPMC, DCPA, alachlor, napropamide, diphenamid, propyzamide, asulam, DCMU, linuron, siduron, dymron, methyl dymron, karbutilate, isouron, simazine, atrazine, propazine, simetryn, ametryn, prometryn, cyanazine, metribuzin, terbacil, bromacil, lenacil, PAC, norflurazon, bentazone, oxadiazon, pyrazolate, paraquat, diquat, trifluralin, benfluralin, nitralin, pendimethalin, MDBA, picloram, TCTP, TCA, tetrapion, amiprofos-methyl, SAP, glyphosate, fosamine-ammonium, bialaphos, glufosinate, ACN, DBN, DCBN, acephenon, alloxydim, chlorphthalim, triclopyl, DSMA, sodium chlorate, sodium cyanate, sodium sulfamate, methy 2- {[(4,6-dimethoxypyrimidine-2-yl)aminocarbonyl]aminosulfonylmethyl} benzoate, 3,7-dichloro-8-quinoline carboxylic acid, N-(1,1-dimethylbenzyl)-2-bromo-t-butylacetamide, 2-(1,3-benzothiazole-2-yl-oxy)-N-methylacetamide and the like.

EXAMPLES OF PLANT GROWTH REGULATING AGENT

Ancymidol, indolebutyric acid, ethychlozate, 2-chloroethyl phosphonic acid, oxyethylene higher alcohol, hydroxyquinolin sulfate, cloxyfonac, chlormequat, dichlorprop, dikegulac, 1-naphthaleneacetamide, nicotinic acid amide, phenoxyacetic acid, benzyl aminopurine, maleic hydrazide, mefluidide and the like.

These pesticidally active ingredients may be used either alone or in a mixture of two or more of them. Common names of the compounds of the above-mentioned pesticidally active ingredients are given in accordance with the "Pesticide Handbook, 1985-version" (published from Zaidan Hojin Nihon Shokubutsu Boeki Kyokai on 30 Jan. 1986).

In carrying out this invention, a method by which fine particles of the hydrophobic substance can be adhered or fixed in the form of a uniform outer layer made of them to or into and over the whole surfaces of individual particles of the pesticidally active ingredient having solid particulate shape, as well as a method by which fine particles of the hydrophobic substance can be applied in the form of a coat-film made of mutually integrated and bound particles of said hydrophobic substance to and over the whole surfaces of the particles of the active ingredient may be used without being limited to particular ones, but these methods may be, for example, the following methods:

(1) A method wherein given amounts of solid particles of a pesticidally active ingredient and fine particles of a hydrophobic substance are placed in a ballmill of centrifugal rotary type and these particulate materials are rotated together with the balls in the mill. In this method using the ball-mill of centrifugal rotary type, the raw materials are rotated together with the balls made of a metal within the mill and are forced to impact against the inner wall of the mill and against the balls, whereby the raw materials are mixed together uniformly, the fine particles of the hydrophobic substance smeare and adhere evenly onto the surfaces of the particles of the pesticidally active ingredient, and the particles of the hydrophobic substance together with the particles of the active ingredient are further subjected to mechanical actions of compression, shearing and impacting, so that individual particles of the finely particulate hydrophobic substance can be rendered to adhere to and over the surfaces of the particles of the pesticidally active ingredient. Or, at the same time as this adhesion or after this adhesion, the individual particles of the hydrophobic substance are partially embedded into the surface layers of the particles of the pesticidally active ingredient to provide such state that the particles of the hydrophobic substance are rooting into the surface layers of the particles of the active ingredient; and thus the particles of the hydrophobic substance are fixed into the particles of the active ingredient. As these processes proceed further, the fine particles of the hydrophobic substance which have been adhered to and/or fixed into the surfaces of the particles of the pesticidally active ingredient can further be subjected to the actions of compression, shearing and impacting as well as the actions of heat of the friction, and as a result, such fine particles of the hydrophobic substance are integrated with each other to form a continuous or cohesive coat-film which surrounds each particle (the core) of the pesticidally active ingredient.

(2) A method of acting the impacting forces in a gas stream flowing at high speed, wherein particles of a pesticidally active ingredient and fine particles of a hydrophobic substance are suspended in their given amounts in a stream of a gas flowing at high speed and these solid particles are then subjected to mechanical actions mainly comprising the impacting forces as produced by collision of the particles, the action of heat of the friction as produced by collision of the particles, and other external application of energy.

In this method, the fine particles of the hydrohobic substance are again subjected to the mechanical actions of compression, shearing and impacting as well as the actions of heat of the friction and thus can be adhered to the surfaces of the particles of the pesticidally active ingredient or fixed into the surfaces of the particles of the active ingredient in the same way as described in the above, and occasionally the processes proceed further until the fine particles of the hydrophobic substance are integrated with each other to form a continuous or cohesive coat-film which surrounds the particle of the active ingredient.

As the devices for working out the above method of acting the impacting forces in high-speed gas stream, there may be used a commerically available "Hybridization System" (a tradename of a device for modifying surfaces of a powdery material in a dry system which is provided from Nara Kikai Seisakujo Co., Ltd.) and a commercially available "Mechanofusion System" (a tradename of a device for fusing surfaces which is provided from Hosokawa Micron Co., Ltd.), and others.

It may be added that heating and cooling can be effected if necessary, when the above-mentioned methods (1) and (2) are worked out.

Pesticide formulations comprising a sustained-releasing pesticide according to this invention may be in the form of dust, DL (driftless) dust, flo-dust, wettable powder, fine granules F, fine granules, granules, suspension concentrates, water-dispersible granules, paste and the like, to which this invention is not limited. Methods for preparation of these formulations may be carried out by mixing the composite particles of the pesticidally active ingredient as obtained according to the present invention with auxiliary additive(s) and filler(s) in a conventional apparatus according to conventional formulation techniques.

The auxiliary additives usable in the formulation of the sustained-releasing pesticide according to the present invention may be a variety of auxiliary additives which have been used conventionally in the preparation of the pesticidal formulations. Examples of such auxiliary additives include anionic surface active agents such as alkyl sulfates, alkylaryl sulfonic acids, alkyl sulfonic acids, polyethylene glycol ethers, polyethylene glycol esters, polyol esters; and non-ionic surface active agents, as well as various kinds of antioxidants, ultraviolet absorbers, inhibitors of hydrolysis, modifiers of physical properties and others.

The fillers which may be used in this invention may also be those which have been used conventionally in the preparation of the pesticidal formulations. Examples of such fillers include mineral materials such as clay, kaoline, sericite zieclite, talc, acidic clay, calcium carbonate, magnesium carbonate, gypsum, diatomaceous earth, pumice, zeolite, perlite, vermiculite, attapulgite and bentonite; natural materials such as starch and cellulose; organic solvents such as xylol, methyl alcohol, ethyl alcohol, isopropyl alcohol, glycerin, ethylene glycol, propylene glycol, propylene glycol monomethylether and methyl naphthalene; and water, etc.

EXAMPLE

This invention is now illustrated with reference to the following Examples to which this invention is not limited. In these Examples, all parts are given by weight.

EXAMPLE 1

Dust

Into a ball-mill of the centrifugal rotary type (a commercially available mixer of the ball-mill type which is sold under a tradename of "Mechanomill" and produced by Okada Seiko Co., Ltd.) were placed 4 parts of kasugamycin powder (with a purity of 72.0% and a mean particle diameter of 30 μm) and 1 part of hydrophobic titanium oxide MT-100S (a tradename of a titanium dioxide treated with aluminum laurate which is produced by Teikoku Kako Co., Ltd. and which is a hydrophobic substance having a mean particle diameter of 0.015 μm and an angle of contact of 145° against water droplet. The mixture of these powders was set at a temperature of 50° C. and mixed for 30 minutes at 400 rpm. In this way, the composite particles of kasugamycin (which were each composed of an outer layer of the hydrophobic titanium dioxide as applied onto the surface of the core particle of kasugamycin) were obtained. 0.35 Parts of the composite particles of kasugamycin (with kasugamycin content of 57.6%), 1.0 part of white carbon, 0.3 parts of isopropyl acid phosphate (a modifier of physical properties) and 98.35 parts of clay were mixed in a hammer-mill to give a dust having the sustained release property and containing 0.2% of kasugamycin.

EXAMPLE 2

Fine granules F

After mixing 0.18 parts of the composite particles of kasugamycin (with kasugamycin content of 57.6%) as prepared in Example 1 with 0.5 parts of a polyvinyl alcohol and 99.32 parts of clay in a hammer-mill, the resulting mixture was added with 5 parts of water and granulated in a tumbling granulator. After drying, the granules were screened and thus adjusted for their granular size (65 to 250 mesh). Fine granules F having the sustained release property and containing 0.1% of kasugamycin were obtained.

EXAMPLE 3

Wettable powder 2.1 Parts of the composite particles of kasugamycin as prepared in Example 1 were mixed with 5 parts of white carbon, 3 parts of sodium lauryl sulfate, 2 parts of calcium ligninsulfonate and 87.9 parts of finely divided clay in a hammer-mill to give a wettable powder having the sustained release property and containing 1.2% of kasugamycin.

EXAMPLE 4

Suspension 2.1 Parts of the composite particles of kasugamycin as prepared in Example 1 were mixed with 15.3 parts of phthalide (with a purity of 98.5%), 2 parts of polyoxyethylene nonyl phenyl ether, 0.2 part of xanthan gum and 70.4 parts of water in a mixer under stirring. A suspension containing 1.2% of kasugamycin and 15% of fthalide was prepared.

EXAMPLE 5

Dust

Using a ball-mill of the centrifugal rotary type (Mechanomill) same as that employed in Example 1, 4 parts of validamycin A (with a purity of 48.5%, and a mean particle diameter of 30 μm) and 1 part of Aerosil R-972 (a tradename of a silicon dioxide treated with dimethylchlorosilane which is produced by Nippon Aerosil Co., Ltd. and which is a hydrophobic substance having a mean particle diameter of 0.016 μm and an angle of contact of 155° against water droplet) were charged in the ball-mill and mixed in the same manner of operation as described in Example 1. There were obtained composite particles of kasugamycin which were each composed of an outer layer of Aerosil R-972 as evenly adhered to and fixed into the surface of the particle of validamycin A.

0.78 Part of the composite particles of validamycin A (with validamycin A content of 38.8%) as prepared in the above were mixed with 1 part of white carbon, 0.3 parts of isopropyl acid phosphate and 97.92 parts of clay in a hammer-mill. A dust having the sustained release property and containing 0.3% of validamycin A was obtained.

EXAMPLE 6

Wettable powder

Using a ball-mill of the centrifugal rotary type (Mechanomill) same as that employed in Example 1, 4 parts of acephate (with a purity of 98.5% and a mean particle diameter of 30 μm) and 1 part of hydrophobic titanium oxide MT-100T (a tradename of a titanium dioxide treated with aluminum stearate which is produced by Teikoku Kako Co., Ltd. and which is a hydrophobic substance having a mean particle diameter of 0.015 μm and an angle of contact of 140° against water droplet) were charged in the ball-mill and mixed for 120 minutes. There were obtained composite particles of acephate which were each composed of an outer layer of the hydrophobic titanium oxide MT-100T (the fine particles of the hydrophobic substance) as evenly adhered onto the surface of the particle of acephate.

63.5 Parts of the composite particles of acephate (with acephate content of 78.8%) as prepared in the above were mixed with 5 parts of white carbon, 2 parts of polyoxyethylene nonyl phenyl ether, 2 parts of calcium ligninsulfonate and 27.5 parts of finely divided clay in a hammer-mill to afford a wettable powder having the sustained release property and containing 50% of acephate.

EXAMPLE 7

Granules

After mixing 6.4 parts of the composite particles of acephate as prepared in Example 6 with 1 part of a polyvinyl alcohol and 92.6 parts of clay in a hammer-mill, the resulting mixture was added with 15 parts of water and kneaded. The kneaded mixture was then granulated in an extruding granulator, and the granules were dried and screened and thus adjusted for their granule size (14 to 32 mesh). Granules having the sustained release property and containing 5% of acephate were obtained.

EXAMPLE 8

Dust

Into a device sold under the tradename of "Hybridization System" were placed 4 parts of NAC (with a purity of 99.0% and a mean particle diameter of 7 μm) and 1 part of Aerosil R-792, followed by operation of the device. There were obtained composite particles of NAC which were each composed of an outer layer of Aerosil R-972 (fine particles of the hydrophobic substance) as evenly applied onto the surface of the particle of NAC.

2.6 Parts of the composite particles of NAC (with an NAC content of 79.2%) were mixed with 1 part of white carbon, 0.3 part of isopropyl acid phosphate and 96.1 parts of clay in a hammer-mill to afford a dust having the sustained release property and containing 2% of NAC.

EXAMPLE 9

Granules

Into a device sold under the tradename of "Hybridization System" were placed 4 parts of bifenox (with a purity of 96.5% and a mean particle diameter of 15 μm) and 1 part of stearic acid (with a mean particle diameter of 3 μm), followed by operation of the device. There were obtained composite particles of bifenox in which the surfaces of the particles of bifenox were coated with a coat-film of stearic acid.

After mixing 6.5 parts of the composite particles of bifenox (with bifenox content of 77.2%) with 5 parts of sodium ligninsulfonate, 20 parts of bentonite and 68.5 parts of clay in a hammer-mill, the resultant mixture was added with 12 parts of water and granulated in a tumbling granulator. After drying, the granules were screened and adjusted for their granule size (14 to 32 mesh) to give granules having the sustained release property and containing 5% of bifenox.

EXAMPLE 10

Dust 0.78 Part of the composite particles of validamycin A as prepared in Example 5, 2.6 parts of the composite particles of NAC as prepared in Example 8, 1 part of white carbon, 0.3 part of isopropyl acid phosphate and 95.32 parts of clay were mixed together in a hammer-mill to obtain a dust having the sustained release property and containing 0.3% of validamycin A and 2% of NAC.

The pesticide having the sustained release property according to this invention may be of some types such as insecticidal agents, fungicidal/bactericidal agents or plant growth regulating agents, etc., according to the nature of the pesticidally active ingredient present therein. Firstly, when the pesticide of this invention is applied to foliages of plants, into soil or into water, this pesticide is able to release the active ingredient gradually therefrom and consequently is able to continue to display the excellent activity sustaining over a prolonged period and exhibit a reduced phytotoxicity to crop plants, as compared to the pesticides having no sustained release property. Secondly, when the amount of the fine particles of the hydrophobic substance as applied to the surfaces of the particles of the pesticidally active ingredient as well as the diameters of these particles and other related conditions are appropriately chosen as described hereinbefore, the rate of release or dissolution of the active ingredient out of the pesticide can be controlled optionally to be increased or decreased. Thirdly, it is readily workable to formulate the sustained-releasing pesticide of this invention by mixing with auxiliary additives, similarly to formulation of conventional pesticide preparations. Fourthly, the sustained-releasing pesticide of this invention can be produced by a dry process without using any solvents, and therefore this invention is applicable to a wide variety of the pesticidally active ingredients and exhibits a wide applicability.

Test Examples are described below to demonstrate the utilities of this invention as described in the above.

Test Example 1

Test for estimating the dissolution-out, namely release of pesticidally active ingredients into water (Test for the sustained release property)

In a flask of 1l-capacity was placed 500 ml of water which has been deionized by ion-exchangers. Into the pool of water in the flask were introduced such composite particles of a pesticidally active ingredient as prepared similarly to the Examples 1, 5, 6, 8, and 9, in such amount that the quantity of the pesticidally active ingredient added was corresponding to 250 mg. Using a testing device for estimating the dissolution-out or release of compounds (of NTR-VS6 type which is provided from Toyama Sangyo Co., Ltd.), the temperature of the water pool was kept at 20° C. and the content of the flask was agitated at 200 rpm. Samples of water were taken out from the flask at pre-determined time intervals, and each sample was assayed to determine the concentration (ppm.) of the active ingredient in the water. Rate (%) of dissolution-out, namely release of the active ingredient was calculated according to the following equation:

$$\text{Rate (\%) of release of active ingredient into water} = \frac{\text{(Concentration of active ingredient at each time of determination)}}{\text{(Theoretical concentration of active ingredient in water when the entire quantity of 250 mg of active ingredient has been released into water)}}$$

These tests for estimating the release of active compound have revealed the following: If the sustained release property is imparted to the composite particles of pesticidally active ingredient, it can be observed that the determined rates (%) of release of active ingredient are less than 100% at the initial stage of the test but the rates of release of active ingredient will increase gradually with lapse of time.

The test results obtained are as shown in Table 1 below. Through these test results, it is evidently found that the pesticide of this invention has been imparted with the sustained release property.

TABLE 1

| Run No. | Fine particles of hydrophobic substance | Particle diameter (μm) of hydrophobic substance | Angle of contact of hydrophobic substance (degree) | Amount of hydrophobic substance used (weight ratio of hydrophobic substance/pesticidally active ingredient | Example | Active ingredient | Rate (%) of Release | | | | |
|---|---|---|---|---|---|---|---|---|---|---|---|
| | | | | | | | After 1 hour | After 2 hours | After 3 hours | After 5 hours | After 24 hours |
| 1 | Titanium oxide MT-100S | 0.015 | 145 | 0.05 | 1 | Kasugamycin | 35 | 42 | 48 | 52 | 56 |
| 2 | Titanium oxide MT-100S | 0.015 | 145 | 0.1 | 1 | Kasugamycin | 30 | 38 | 43 | 48 | 50 |
| 3 | Titanium oxide MT-100S | 0.015 | 145 | 0.25 | 1 | Kasugamycin | 27 | 35 | 41 | 45 | 47 |
| 4 | Titanium oxide MT-100S | 0.015 | 145 | 0.5 | 1 | Kasugamycin | 20 | 32 | 39 | 42 | 44 |
| 5 | Titanium oxide MT-100S | 0.015 | 145 | 1.0 | 1 | Kasugamycin | 15 | 27 | 34 | 40 | 41 |
| 6 | Titanium oxide MT-100S | 0.015 | 145 | 0.05 | 5 | Validamycin A | 9 | 14 | 17 | 20 | 23 |
| 7 | Titanium oxide MT-100S | 0.015 | 145 | 0.25 | 5 | Validamycin A | 6 | 10 | 12 | 16 | 18 |
| 8 | Titanium oxide MT-100S | 0.015 | 145 | 0.5 | 5 | Validamycin A | 5 | 8 | 10 | 12 | 15 |
| 9 | Titanium oxide MT-100S | 0.015 | 145 | 1.0 | 5 | Validamycin A | 3 | 5 | 7 | 10 | 12 |
| 10 | Titanium oxide MT-100S | 0.015 | 145 | 0.05 | 8 | NAC | 27 | 32 | 36 | 36 | 39 |
| 11 | Titanium oxide MT-100S | 0.015 | 145 | 0.25 | 8 | NAC | 23 | 28 | 31 | 31 | 35 |
| 12 | Titanium oxide MT-100S | 0.015 | 145 | 0.5 | 8 | NAC | 20 | 25 | 28 | 30 | 33 |
| 13 | Titanium oxide MT-100S | 0.015 | 145 | 1.0 | 8 | NAC | 18 | 22 | 23 | 25 | 29 |
| 14 | Titanium oxide MT-100T | 0.015 | 140 | 0.05 | 6 | Acephate | 34 | 43 | 48 | 52 | 56 |
| 15 | Titanium oxide MT-100T | 0.015 | 140 | 1.0 | 6 | Acephate | 31 | 40 | 44 | 48 | 52 |
| 16 | Titanium oxide MT-100T | 0.015 | 140 | 0.25 | 6 | Acephate | 27 | 38 | 43 | 45 | 49 |
| 17 | Titanium oxide MT-100T | 0.015 | 140 | 0.5 | 6 | Acephate | 24 | 35 | 40 | 41 | 45 |
| 18 | Titanium oxide MT-100T | 0.015 | 140 | 1.0 | 6 | Acephate | 19 | 30 | 34 | 36 | 41 |
| 19 | Titanium oxide MT-100T | 0.015 | 140 | 0.05 | 1 | Kasugamycin | 31 | 34 | 39 | 46 | 52 |
| 20 | Titanium oxide MT-100T | 0.015 | 140 | 0.25 | 1 | Kasugamycin | 26 | 30 | 35 | 41 | 49 |
| 21 | Titanium oxide MT-100T | 0.015 | 140 | 0.5 | 1 | Kasugamycin | 23 | 27 | 32 | 38 | 45 |
| 22 | Titanium oxide MT-100T | 0.015 | 140 | 1.0 | 1 | Kasugamycin | 18 | 21 | 27 | 32 | 39 |
| 23 | Titanium oxide MT-100T | 0.015 | 140 | 0.05 | 9 | Bifenox | 18 | 19 | 22 | 25 | 33 |
| 24 | Titanium oxide MT-100T | 0.015 | 140 | 0.25 | 9 | Bifenox | 15 | 18 | 20 | 22 | 28 |
| 25 | Titanium oxide MT-100T | 0.015 | 140 | 0.5 | 9 | Bifenox | 10 | 13 | 15 | 17 | 24 |
| 26 | Titanium oxide MT-100T | 0.015 | 140 | 1.0 | 9 | Bifenox | 9 | 10 | 11 | 12 | 18 |
| 27 | Aerosil R-972 | 0.016 | 155 | 0.05 | 5 | Validamycin A | 7 | 9 | 10 | 13 | 16 |
| 28 | Aerosil R-972 | 0.016 | 155 | 0.1 | 5 | Validamycin A | 2 | 5 | 6 | 7 | 8 |
| 29 | Aerosil R-972 | 0.016 | 155 | 0.25 | 5 | Validamycin A | 1 | 3 | 3 | 4 | 5 |
| 30 | Aerosil R-972 | 0.016 | 155 | 0.5 | 5 | Validamycin A | 1 | 2 | 3 | 4 | 5 |
| 31 | Aerosil R-972 | 0.016 | 155 | 1.0 | 5 | Validamycin A | 1 | 2 | 3 | 4 | 5 |
| 32 | Aerosil R-972 | 0.016 | 155 | 0.05 | 1 | Kasugamycin | 11 | 13 | 15 | 18 | 28 |
| 33 | Aerosil R-972 | 0.016 | 155 | 0.25 | 1 | Kasugamycin | 6 | 9 | 10 | 14 | 23 |
| 34 | Aerosil R-972 | 0.016 | 155 | 0.5 | 1 | Kasugamycin | 5 | 8 | 9 | 12 | 19 |
| 35 | Aerosil R-972 | 0.016 | 155 | 1.0 | 1 | Kasugamycin | 5 | 8 | 7 | 9 | 15 |
| 36 | Aerosil R-972 | 0.016 | 155 | 0.05 | 8 | NAC | 29 | 41 | 51 | 53 | 59 |
| 37 | Aerosil R-972 | 0.016 | 155 | 0.25 | 8 | NAC | 24 | 36 | 46 | 48 | 53 |
| 38 | Aerosil R-972 | 0.016 | 155 | 0.5 | 8 | NAC | 20 | 33 | 42 | 43 | 49 |
| 39 | Aerosil R-972 | 0.016 | 155 | 1.0 | 8 | NAC | 15 | 28 | 37 | 39 | 44 |
| 40 | Stearic acid | 3.0 | 90 | 0.05 | 9 | Bifenox | 36 | 41 | 44 | 47 | 52 |
| 41 | Stearic acid | 3.0 | 90 | 0.1 | 9 | Bifenox | 30 | 35 | 38 | 39 | 45 |
| 42 | Stearic acid | 3.0 | 90 | 0.25 | 9 | Bifenox | 28 | 32 | 34 | 36 | 42 |
| 43 | Stearic acid | 3.0 | 90 | 0.5 | 9 | Bifenox | 25 | 29 | 30 | 33 | 39 |
| 44 | Stearic acid | 3.0 | 90 | 1.0 | 9 | Bifenox | 20 | 23 | 24 | 28 | 36 |
| 45 | Stearic acid | 3.0 | 90 | 0.05 | 6 | Acephate | 33 | 38 | 42 | 49 | 58 |
| 46 | Stearic acid | 3.0 | 90 | 0.25 | 6 | Acephate | 30 | 34 | 37 | 42 | 51 |
| 47 | Stearic acid | 3.0 | 90 | 0.5 | 6 | Acephate | 28 | 32 | 35 | 39 | 49 |
| 48 | Stearic acid | 3.0 | 90 | 1.0 | 6 | Acephate | 27 | 30 | 31 | 35 | 42 |

TABLE 1-continued

| Run No. | Fine particles of hydrophobic substance | Particle diameter (μm) of hydrophobic substance | Angle of contact of hydrophobic substance (degree) | Amount of hydrophobic substance used (weight ratio of hydrophobic substance/pesticidally active ingredient | Example | Active ingredient | Rate (%) of Release | | | | | |
|---|---|---|---|---|---|---|---|---|---|---|---|---|
| | | | | | | | After 1 hour | After 2 hours | After 3 hours | After 5 hours | After 24 hours |
| 49 | Palmitic acid | 5.0 | 85 | 0.05 | 1 | Kasugamycin | 36 | 39 | 42 | 47 | 56 |
| 50 | Palmitic acid | 5.0 | 85 | 0.1 | 1 | Kasugamycin | 31 | 35 | 36 | 42 | 50 |
| 51 | Palmitic acid | 5.0 | 85 | 0.25 | 1 | Kasugamycin | 29 | 32 | 34 | 39 | 47 |
| 52 | Palmitic acid | 5.0 | 85 | 0.5 | 1 | Kasugamycin | 26 | 30 | 31 | 36 | 44 |
| 53 | Palmitic acid | 5.0 | 85 | 1.0 | 1 | Kasugamycin | 21 | 25 | 27 | 31 | 40 |
| 54 | Lauric acid | 5.0 | 90 | 0.05 | 5 | Validamycin A | 19 | 20 | 22 | 28 | 34 |
| 55 | Lauric acid | 5.0 | 90 | 0.1 | 5 | Validamycin A | 14 | 15 | 18 | 22 | 28 |
| 56 | Lauric acid | 5.0 | 90 | 0.25 | 5 | Validamycin A | 12 | 14 | 17 | 19 | 25 |
| 57 | Lauric acid | 5.0 | 90 | 0.5 | 5 | Validamycin A | 10 | 11 | 14 | 16 | 22 |
| 58 | Lauric acid | 5.0 | 90 | 1.0 | 5 | Validamycin A | 7 | 8 | 9 | 12 | 19 |
| 59 | Myristic acid | 1.0 | 75 | 0.05 | 8 | NAC | 35 | 37 | 41 | 43 | 54 |
| 60 | Myristic acid | 1.0 | 75 | 0.1 | 8 | NAC | 30 | 32 | 35 | 38 | 46 |
| 61 | Myristic acid | 1.0 | 75 | 0.25 | 8 | NAC | 27 | 29 | 31 | 35 | 41 |
| 62 | Myristic acid | 1.0 | 75 | 0.5 | 8 | NAC | 24 | 26 | 28 | 32 | 38 |
| 63 | Myristic acid | 1.0 | 75 | 1.0 | 8 | NAC | 20 | 21 | 23 | 25 | 32 |
| 64 | Aluminum stearate | 2.5 | 130 | 0.05 | 1 | Kasugamycin | 39 | 44 | 46 | 50 | 59 |
| 65 | Aluminum stearate | 2.5 | 130 | 0.1 | 1 | Kasugamycin | 35 | 39 | 42 | 45 | 54 |
| 66 | Aluminum stearate | 2.5 | 130 | 0.25 | 1 | Kasugamycin | 32 | 35 | 38 | 40 | 48 |
| 67 | Aluminum stearate | 2.5 | 130 | 0.5 | 1 | Kasugamycin | 29 | 33 | 35 | 36 | 44 |
| 68 | Aluminum stearate | 2.5 | 130 | 1.0 | 1 | Kasugamycin | 24 | 28 | 30 | 31 | 39 |
| 69 | Aluminum stearate | 2.5 | 130 | 0.05 | 9 | Bifenox | 24 | 28 | 30 | 34 | 47 |
| 70 | Aluminum stearate | 2.5 | 130 | 0.25 | 9 | Bifenox | 22 | 25 | 27 | 31 | 40 |
| 71 | Aluminum stearate | 2.5 | 130 | 0.5 | 9 | Bifenox | 18 | 22 | 23 | 27 | 35 |
| 72 | Aluminum stearate | 2.5 | 130 | 1.0 | 9 | Bifenox | 13 | 15 | 18 | 20 | 30 |
| 73 | Magnesium stearate | 4.0 | 120 | 0.05 | 5 | Validamycin A | 28 | 30 | 32 | 34 | 41 |
| 74 | Magnesium stearate | 4.0 | 120 | 0.1 | 5 | Validamycin A | 23 | 25 | 27 | 29 | 35 |
| 75 | Magnesium stearate | 4.0 | 120 | 0.25 | 5 | Validamycin A | 20 | 22 | 24 | 27 | 33 |
| 76 | Magnesium stearate | 4.0 | 120 | 0.5 | 5 | Validamycin A | 18 | 20 | 22 | 24 | 36 |
| 77 | Magnesium stearate | 4.0 | 120 | 1.0 | 5 | Validamycin A | 13 | 16 | 17 | 19 | 29 |
| 78 | Calcium stearate | 1.0 | 140 | 0.05 | 8 | NAC | 34 | 38 | 42 | 46 | 57 |
| 79 | Calcium stearate | 1.0 | 140 | 0.1 | 8 | NAC | 30 | 32 | 37 | 39 | 48 |
| 80 | Calcium stearate | 1.0 | 140 | 0.25 | 8 | NAC | 26 | 29 | 33 | 35 | 44 |
| 81 | Calcium stearate | 1.0 | 140 | 0.5 | 8 | NAC | 24 | 27 | 30 | 32 | 46 |
| 82 | Calcium stearate | 1.0 | 140 | 1.0 | 8 | NAC | 20 | 22 | 25 | 28 | 40 |
| 83 | Polystyrene resin | 5.0 | 115 | 0.05 | 6 | Acephate | 39 | 45 | 49 | 54 | 60 |
| 84 | Polystyrene resin | 5.0 | 115 | 0.1 | 6 | Acephate | 35 | 40 | 44 | 48 | 55 |
| 85 | Polystyrene resin | 5.0 | 115 | 0.25 | 6 | Acephate | 32 | 37 | 41 | 45 | 51 |
| 86 | Polystyrene resin | 5.0 | 115 | 0.5 | 6 | Acephate | 30 | 34 | 37 | 41 | 48 |
| 87 | Polystyrene resin | 5.0 | 115 | 1.0 | 6 | Acephate | 25 | 29 | 32 | 36 | 43 |
| 88 | Polyamide resin | 5.0 | 125 | 0.05 | 1 | Kasugamycin | 22 | 24 | 26 | 31 | 40 |
| 89 | Polyamide resin | 5.0 | 125 | 0.1 | 1 | Kasugamycin | 27 | 29 | 32 | 37 | 46 |
| 90 | Polyamide resin | 5.0 | 125 | 0.25 | 1 | Kasugamycin | 29 | 32 | 34 | 39 | 48 |
| 91 | Polyamide resin | 5.0 | 125 | 0.5 | 1 | Kasugamycin | 26 | 30 | 31 | 37 | 45 |
| 92 | Polyamide resin | 5.0 | 125 | 1.0 | 1 | Kasugamycin | 25 | 27 | 29 | 30 | 40 |
| 93 | Silicone resin | 2.0 | 150 | 0.05 | 9 | Bifenox | 12 | 15 | 18 | 19 | 26 |
| 94 | Silicone resin | 2.0 | 150 | 0.1 | 9 | Bidenox | 17 | 20 | 22 | 24 | 30 |
| 95 | Silicone resin | 2.0 | 150 | 0.25 | 9 | Bifenox | 14 | 17 | 18 | 20 | 26 |
| 96 | Silicone resin | 2.0 | 150 | 0.5 | 9 | Bifenox | 11 | 12 | 13 | 16 | 23 |

TABLE 1-continued

| Run No. | Fine particles of hydrophobic substance | Particle diameter (μm) of hydrophobic substance | Angle of contact of hydrophobic substance (degree) | Amount of hydrophobic substance used (weight ratio of hydrophobic substance/pesticidally active ingredient | Example | Active ingredient | Rate (%) of Release After 1 hour | After 2 hours | After 3 hours | After 5 hours | After 24 hours |
|---|---|---|---|---|---|---|---|---|---|---|---|
| 97 | Silicone resin | 2.0 | 150 | 1.0 | 9 | Bifenox | 9 | 10 | 11 | 13 | 18 |
| 98 | No use (an active ingredient alone used) | — | — | — | Comparative Example 1 | Kasugamycin | 100 | | | | |
| 99 | No use (an active ingredient alone used) | — | — | — | Comparative Example 2 | Validamycin A | 100 | | | | |
| 100 | No use (an active ingredient alone used) | — | — | — | Comparative Example 3 | NAC | 100 | | | | |
| 101 | No use (an active ingredient alone used) | — | — | — | Comparative Example 4 | Acephate | 100 | | | | |
| 102 | No use (an active ingredient alone used) | — | — | — | Comparative Example 5 | Bifenox | 100 | | | | |
| 103 | Titanium oxide MT-100S | 0.015 | 145 | 0.03 | Comparative Example 6 (1) | Kasugamycin | 85 | 93 | 100 | | |
| 104 | Titanium oxide MT-100S | 0.015 | 145 | 0.03 | Comparative Example 7 (5) | Validamycin A | 80 | 86 | 92 | 100 | |
| 105 | Titanium oxide MT-100S | 0.015 | 145 | 0.03 | Comparative Example 8 (8) | NAC | 86 | 95 | 100 | | |
| 106 | Titanium oxide MT-100T | 0.015 | 140 | 0.03 | Comparative Example 9 (6) | Acephate | 88 | 96 | 100 | | |
| 107 | Titanium oxide MT-100T | 0.015 | 140 | 0.03 | Comparative Example 10 (1) | Kasugamycin | 87 | 98 | 100 | | |
| 108 | Titanium oxide MT-100T | 0.015 | 140 | 0.03 | Comparative Example 11 (9) | Bifenox | 82 | 86 | 94 | 100 | |
| 109 | Aerosil R-972 | 0.016 | 155 | 0.03 | Comparative Example 12 (5) | Validamycin A | 74 | 80 | 86 | 94 | 100 |
| 110 | Aerosil R-972 | 0.016 | 155 | 0.03 | Comparative Example 13 (1) | Kasugamycin | 78 | 82 | 88 | 97 | 100 |
| 111 | Aerosil R-972 | 0.016 | 155 | 0.03 | Comparative Example 14 (8) | NAC | 84 | 92 | 100 | | |
| 112 | Stearic acid | 3.0 | 90 | 0.03 | Comparative Example 15 (9) | Bifenox | 90 | 100 | | | |
| 113 | Stearic acid | 10.0 | 90 | 0.03 | Comparative Example 16 (6) | Acephate | 92 | 100 | | | |
| 114 | Palmitic acid | 5.0 | 85 | 0.25 | Comparative Example 17 (1) | Kasugamycin | 89 | 100 | | | |
| 115 | Palmitic acid | 7.0 | 85 | 0.25 | Comparative | Kasugamycin | 94 | 100 | | | |

TABLE 1-continued

| Run No. | Fine particles of hydrophobic substance | Particle diameter (μm) of hydrophobic substance | Angle of contact of hydrophobic substance (degree) | Amount of hydrophobic substance used (weight ratio of hydrophobic substance/pesticidally active ingredient | Example | Active ingredient | Rate (%) of Release | | | | |
|---|---|---|---|---|---|---|---|---|---|---|---|
| | | | | | | | After 1 hour | After 2 hours | After 3 hours | After 5 hours | After 24 hours |
| | | | | | Example 18 (1) | | | | | | |
| 116 | Lauric acid | 8.0 | 90 | 0.25 | Comparative Example 19 (5) | Validamycin A | 92 | 100 | | | |
| 117 | Aluminum stearate | 8.0 | 130 | 0.25 | Comparative Example 20 (1) | Kasugamycin A | 88 | 94 | 100 | | |
| 118 | Magnesium stearate | 8.0 | 120 | 0.25 | Comparative Example 21 (5) | Validamycin A | 86 | 92 | 100 | | |
| 119 | Polystyrene resin | 7.0 | 115 | 0.25 | Comparative Example 22 (6) | Acephate | 82 | 90 | 100 | | |
| 120 | Titanium dioxide | 0.015 | 60 | 0.25 | Comparative Example 23 (1) | Kasugamycin | 100 | | | | |
| 121 | Titanium dioxide | 0.015 | 60 | 0.25 | Comparative Example 24 (5) | Validamycin A | 100 | | | | |
| 122 | Titanium dioxide | 0.015 | 60 | 0.25 | Comparative Example 25 (6) | Acephate | 100 | | | | |
| 123 | Titanium dioxide | 0.015 | 60 | 0.25 | Comparative Example 26 (9) | Bifenox | 100 | | | | |
| 124 | Silicon dioxide | 0.012 | 20 | 0.25 | Comparative Example 27 (1) | Kasugamycin | 100 | | | | |
| 125 | Silicon dioxide | 0.012 | 20 | 0.25 | Comparative Example 28 (8) | NAC | 100 | | | | |
| 126 | Methacrylate resin | 0.4 | 65 | 0.25 | Comparative Example 29 (1) | Kasugamycin | 100 | | | | |
| 127 | Methacrylate resin | 0.4 | 65 | 0.25 | Comparative Example 30 (6) | Acephate | 100 | | | | |

Note 1: In comparative Examples 1 to 5, a bulk powder of the active ingredient compound was tested alone as such in the tests for estimating the release of active compound.
Note 2: Number given in the brackets shown below comparative Examples 6 to 30 denotes that composite particles tested there were prepared in a similar manner to the procedures of Examples having the corresponding Number.

TEST EXAMPLE 2

Tests for estimating the effects of controlling blast disease in rice plant (for confirmation of the sustaining of the fungicidal activity)

Seeds of a rice plant (Variety: Akihikari) were immersed in water until the seeds begun to germinate. These seeds were then sown along lines in a farm field which was prepared in a greenhouse made of polyvinyl chloride resin.

On 28 days after the seed sowing, the young seedlings of rice plant at the three-leaf stage were treated by applying thereto a dust preparation having the sustained release property which contained the composite particles of kasugamycin as prepared similarly to Example 1. This application of the dust preparation was made at a rate of application of 3 kg/10 ares of the dust with using a simple device for application of a dust preparation. On the other hand, another leave of rice plant were inoculated with the phytopathogenic fungus of rice blast disease (*Pyricularia oryzae*) and incubated to a stage of formation of spores, and the resultant fungally infected leave were cut into pieces of about 3 cm-squares. These pieces of the infected leave were scattered and placed over the entire area of the test plots 2 days after the application of the dust preparation and served to act as the source of inoculation, while the rice plants were always kept under such conditions that they were susceptible of being infected with the rice blast disease. Within the greenhouse, there were always existing a moisture. The estimation of the infection was made in such a way that the rate (%) of the area of infection of the rice blast disease on the leave of rice plant (against the total area of the leave of rice plant) were measured with lapse of time at intervals of 3 to 4 days from 7 days after the fungal inoculation and that rates (%) of disease control were evaluated according to the following equation:

$$\text{Rate (\%) of Disease Control} = \left(1 - \frac{\text{Rate of the area of infection in treated plots}}{\text{Rate of the area of infection in untreated plots}}\right) \times 100$$

These tests were carried out in three-replicates with each test plot of 1 m$^2$ in area, and an averaged value of the rates (%) of disease control was calculated.

As the comparative agent was tested such a dust preparation having no sustained release property which was prepared by using an untreated bulk powder of kasugamycin in place of the composite particles of kasugamycin of Example 1.

The results are shown in Table 2 below.

TABLE 2

| Run No. | Fine particles of hydrophobic substance | Particle diameter (μm) of hydrophobic substance | Angle of contact of hydrophobic substance (degree) | Amount of hydrophobic substance used (weight ratio of hydrophobic substance/pesticidally active ingredient) | Rate (%) of Disease Control 7 days after inoculation | 11 days after inoculation | 14 days after inoculation | 17 days after inoculation | 20 days after inoculation | Phytotoxicity |
|---|---|---|---|---|---|---|---|---|---|---|
| 1 | Titanium oxide MT-100S | 0.015 | 145 | 0.05 | 95 | 93 | 90 | 85 | 60 | Not observed |
| 2 | Titanium oxide MT-100S | 0.015 | 145 | 0.25 | 95 | 93 | 90 | 85 | 59 | Not observed |
| 3 | Titanium oxide MT-100S | 0.015 | 145 | 0.5 | 94 | 92 | 91 | 84 | 62 | Not observed |
| 4 | Titanium oxide MT-100S | 0.015 | 145 | 1.0 | 95 | 92 | 91 | 85 | 62 | Not observed |
| 5 | Aerosil R-972 | 0.016 | 155 | 0.05 | 96 | 94 | 91 | 82 | 63 | Not observed |
| 6 | Aerosil R-972 | 0.016 | 155 | 0.25 | 95 | 93 | 90 | 86 | 62 | Not observed |
| 7 | Aerosil R-972 | 0.016 | 155 | 0.5 | 94 | 92 | 90 | 85 | 62 | Not observed |
| 8 | Aerosil R-972 | 0.016 | 155 | 1.0 | 94 | 92 | 90 | 85 | 62 | Not observed |
| 9 | Palmitic acid | 5.0 | 85 | 0.05 | 95 | 93 | 89 | 82 | 63 | Not observed |
| 10 | Palmitic acid | 5.0 | 85 | 0.25 | 95 | 93 | 90 | 83 | 60 | Not observed |
| 11 | Palmitic acid | 5.0 | 85 | 0.5 | 96 | 94 | 90 | 86 | 59 | Not observed |
| 12 | Palmitic acid | 5.0 | 85 | 1.0 | 96 | 93 | 91 | 86 | 60 | Not observed |
| 13 | Aluminum stearate | 2.5 | 130 | 0.05 | 95 | 92 | 89 | 85 | 60 | Not observed |
| 14 | Aluminum stearate | 2.5 | 130 | 0.25 | 95 | 92 | 89 | 85 | 62 | Not observed |
| 15 | Aluminum stearate | 2.5 | 130 | 0.5 | 95 | 92 | 90 | 82 | 62 | Not observed |
| 16 | Aluminum stearate | 2.5 | 130 | 1.0 | 94 | 91 | 90 | 81 | 62 | Not observed |
| 17 | Polyamide resin | 5.0 | 125 | 0.05 | 96 | 94 | 90 | 82 | 59 | Not observed |
| 18 | Polyamide resin | 5.0 | 125 | 0.25 | 96 | 93 | 89 | 85 | 60 | Not observed |
| 19 | Polyamide resin | 5.0 | 125 | 0.5 | 95 | 93 | 90 | 85 | 60 | Not observed |

TABLE 2-continued

| Run No. | Fine particles of hydrophobic substance | Particle diameter (μm) of hydrophobic substance | Angle of contact of hydrophobic substance (degree) | Amount of hydrophobic substance used (weight ratio of hydrophobic substance/pesticidally active ingredient) | Rate (%) of Disease Control | | | | | Phytotoxicity |
|---|---|---|---|---|---|---|---|---|---|---|
| | | | | | 7 days after inoculation | 11 days after inoculation | 14 days after inoculation | 17 days after inoculation | 20 days after inoculation | |
| 20 | Polyamide resin | 5.0 | 125 | 1.0 | 95 | 93 | 90 | 84 | 60 | Not observed |
| 21 | Comparative agent | — | — | — | 95 | 85 | 65 | 40 | 20 | Not observed |
| 22 | Untreated plot | — | — | — | 0 (13) | 0 (34) | 0 (58) | 0 (84) | 0 (95) | — |

Note: Numerical figures given in the brackets for the tests of the untreated plot denote such rate (%) of the area of infection as evaluated in the untreated plot.

Test Example 3

Tests for estimating the effect of controlling sheath blight disease in rice plant (for confirmation of the sustaining of the fungicidal activity)

Rice plants (Variety: Nihonbare, ten rice plants per pot and at 5 to 6-foliage stage) which had been cultivated in pots of 9 cm in diameter were treated by applying thereto such a dust preparation having the sustained release property which contained the composite particles of validamycin A as prepared similarly to Example 5. This application of the dust preparations was done at a rate of application of 3 kg/10 ares of the dust with using a simple device for application of a dust. On the other hand, a phytopathogenic fungus of rice sheath blight disease (*Rhizoctonia solani*) was incubated for 7 days (at 28° C.) in a culture medium comprising wheat bran and further containing 0.5% peptone added, so that the fungal culture was obtained. One gram of this fungal culture was used as an inoculum and placed on the soil at the bases of the rice plants in each pot at a time of 3 days, 7 days or 15 days after the application of the dust preparation. After the inoculation, rice plants were maintained at 28°-30° C. for 10 days within a greenhouse for development of the infection, where a humidity of not lower than 90% was prevailing. Thereafter, the rice plants were removed out of the greenhouse and the length (cm) (an averaged value) of the lesions of infection of rice sheath blight disease on the leave of rice plant was measured. Rate (%) of disease control was calculated according to the following equation:

$$\text{Rate (\%) of disease control} = \left(1 - \frac{\text{Length of the lesions of infection in treated plot}}{\text{Length of the lesions of infection in untreated plot}}\right) \times 100$$

These tests were carried out in three-replicates, and an averaged value of the rates (%) of disease control was calculated.

As comparative agent was tested such a dust preparation having no sustained release property which was prepared in the same manner as in Example 5 but using an untreated bulk powder of validamycin A in place of the composite particles of validamycin A of Example 5.

The results are shown in Table 3.

TABLE 3

| Run No. | Fine particles of hydrophobic substance | Particle diameter (μm) of hydrophobic substance | Angle of contact of hydrophobic substance (degree) | Amount of hydrophobic substance used (weight ratio of hydrophobic substance/pesticidally active ingredient) | Rate (%) of Disease Control | | | Phytotoxicity |
|---|---|---|---|---|---|---|---|---|
| | | | | | After 3 days | After 7 days | After 15 days | |
| 1 | Titanium oxide MT-100S | 0.015 | 145 | 0.05 | 100 | 90 | 60 | Not observed |
| 2 | Titanium oxide MT-100S | 0.015 | 145 | 0.25 | 99 | 89 | 65 | Not observed |
| 3 | Titanium oxide MT-100S | 0.015 | 145 | 0.5 | 99 | 90 | 60 | Not observed |
| 4 | Titanium oxide MT-100S | 0.015 | 145 | 1.0 | 99 | 90 | 58 | Not observed |
| 5 | Aerosil R-972 | 0.016 | 155 | 0.05 | 99 | 85 | 62 | Not observed |
| 6 | Aerosil R-972 | 0.016 | 155 | 0.25 | 100 | 87 | 65 | Not observed |
| 7 | Aerosil R-972 | 0.016 | 155 | 0.5 | 99 | 90 | 65 | Not observed |
| 8 | Aerosil R-972 | 0.016 | 155 | 1.0 | 99 | 90 | 62 | Not observed |
| 9 | Comparative agent | — | — | — | 99 | 30 | 5 | Not observed |
| 10 | Untreated plot | — | — | — | 0 (16.5) | 0 (16.6) | 0 (16.7) | — |

Note: Numberical figures given in the brackets for the tests of the untreated plot denote such average value of lengths (cm) of the lesions of infection as evaluated in the untreated plot.

Test Example 4

Test for estimating the sustaining property of the isecticidal activity against cabbage spinach aphis Cabbage plants (Variety: Chyusosei, at 10 to 11-foliage stage) which were cultivated in pots were treated by spraying thereto such a test liquid which had been prepared by diluting with water such a wettable powder having the sustained release property and containing the composite particles of Acephate as produced similarly to Example 6. The dilution of the wettable powder with water was conducted using the volumes of water which were such many times as much as the volume of the wettable powder as corresponding to the times of dilution (folds) given in Table 4. The spraying application of the test liquid was made at a rate of application of 150 l/are by means of a spray-gun while the cabbage plants were placed on a turning table. Thereafter, the cabbage plants treated were placed in a glass chamber. Several days later, the leaf of cabbage plants was cut into pieces of leaf by means of a leaf-puncher of 8 cm in diameter. The pieces of leaf were placed in a dish made of a plastic resin and having a diameter of 9 cm, along with adults of spinach aphis (*Myzus persica*) of apterous forms. The insects were left to move in the dish for 48 hours at a constant temperature of 25° C., and thereafter the rates (%) of the insects killed was evaluated with lapsed time.

These tests were carried out in three-replicates, and an averaged value of the rates (%) of the insects killed was calculated.

As comparative agent was tested such a wettable powder having no sustained release property which was prepared in the same manner as in Example 6 but using an untreated bulk powder of Acephate in place of the composite particles of Acephate of Example 6.

The results are shown in Table 4.

TABLE 4

| Run No. | Fine particles of hydrophobic substance | Particle diameter (μm) of hydrophobic substance | Angle of contact of hydrophobic substance (degree) | Amount of hydrophobic substance used (weight ratio of hydrophobic substance/pesticidally active ingredient) | Times of dilution (folds) | Rate (%) of insects killed | | | | | Phytotoxicity |
|---|---|---|---|---|---|---|---|---|---|---|---|
| | | | | | | after treatment | After 7 days | After 14 days | After 21 days | After 28 days | |
| 1 | Titanium oxide MT-100T | 0.015 | 140 | 0.05 | 1000 | 100 | 100 | 100 | 100 | 93 | Not observed |
| 2 | Titanium oxide MT-100T | 0.015 | 140 | 0.05 | 2000 | 100 | 100 | 100 | 97 | 83 | Not observed |
| 3 | Titanium oxide MT-100T | 0.015 | 140 | 0.05 | 4000 | 100 | 100 | 93 | 70 | 50 | Not observed |
| 4 | Titanium oxide MT-100T | 0.015 | 140 | 0.25 | 1000 | 100 | 100 | 100 | 100 | 93 | Not observed |
| 5 | Titanium oxide MT-100T | 0.015 | 140 | 0.25 | 2000 | 100 | 100 | 100 | 97 | 83 | Not observed |
| 6 | Titanium oxide MT-100T | 0.015 | 140 | 0.25 | 4000 | 100 | 100 | 97 | 67 | 47 | Not observed |
| 7 | Titanium oxide MT-100T | 0.015 | 140 | 0.5 | 1000 | 100 | 100 | 100 | 100 | 93 | Not observed |
| 8 | Titanium oxide MT-100T | 0.015 | 140 | 0.5 | 2000 | 100 | 100 | 100 | 97 | 77 | Not observed |
| 9 | Titanium oxide MT-100T | 0.015 | 140 | 0.5 | 4000 | 100 | 100 | 97 | 70 | 47 | Not observed |
| 10 | Titanium oxide MT-100T | 0.015 | 140 | 1.0 | 1000 | 100 | 100 | 100 | 100 | 97 | Not observed |
| 11 | Titanium oxide MT-100T | 0.015 | 140 | 1.0 | 2000 | 100 | 100 | 100 | 97 | 83 | Not observed |
| 12 | Titanium oxide MT-100T | 0.015 | 140 | 1.0 | 4000 | 100 | 100 | 97 | 80 | 50 | Not observed |
| 13 | Aerosil R-972 | 0.016 | 155 | 0.25 | 1000 | 100 | 100 | 100 | 100 | 93 | Not observed |
| 14 | Aerosil R-972 | 0.016 | 155 | 0.25 | 2000 | 100 | 100 | 100 | 97 | 80 | Not observed |
| 15 | Aerosil R-972 | 0.016 | 155 | 0.25 | 4000 | 100 | 100 | 97 | 63 | 43 | Not observed |
| 16 | Stearic acid | 3.0 | 90 | 0.25 | 1000 | 100 | 100 | 100 | 97 | 90 | Not observed |
| 17 | Stearic acid | 3.0 | 90 | 0.25 | 2000 | 100 | 100 | 100 | 93 | 77 | Not observed |
| 18 | Stearic acid | 3.0 | 90 | 0.25 | 4000 | 100 | 100 | 97 | 77 | 50 | Not observed |
| 19 | Polystyrene resin | 5.0 | 115 | 0.25 | 1000 | 100 | 100 | 100 | 100 | 93 | Not observed |
| 20 | Polystyrene resin | 5.0 | 115 | 0.25 | 2000 | 100 | 100 | 100 | 97 | 83 | Not observed |
| 21 | Polystyrene resin | 5.0 | 115 | 0.25 | 4000 | 100 | 100 | 97 | 93 | 45 | Not observed |
| 22 | Comparative agent | — | — | — | 1000 | 100 | 100 | 97 | 63 | 30 | Not observed |

TABLE 4-continued

| Run No. | Fine particles of hydrophobic substance | Particle diameter (μm) of hydrophobic substance | Angle of contact of hydrophobic substance (degree) | Amount of hydrophobic substance used (weight ratio of hydrophobic substance/pesticidally active ingredient) | Times of dilution (folds) | Rate (%) of insects killed | | | | | Phytotoxicity |
|---|---|---|---|---|---|---|---|---|---|---|---|
| | | | | | | after treatment | After 7 days | After 14 days | After 21 days | After 28 days | |
| 23 | Comparative agent | — | — | — | 2000 | 100 | 100 | 70 | 37 | 10 | Not observed |
| 24 | Comparative agent | — | — | — | 4000 | 100 | 83 | 43 | 7 | 0 | Not observed |
| 25 | Untreated plot | — | — | — | — | 0 | 0 | 3 | 0 | 3 | — |

Test Example 5

Tests for estimating the sustaining character of the insecticidal activity against small brown planthopper Rice plants (Variety: Nihonbare) were cultivated in pots having a diameter of 11 cm with five rice plants being grown together in the form of a bundle or stock in each pot, and the cultivated rice plants at 4-leaf stage were treated by applying to them a dust preparation having the sustained release property which contained the composite particles of NAC as produced similarly to Example 8. This application of the dust preparation was made at a rate of application of 3 kg/10 ares of the dust by means of Midget-duster. After this, the rice plants treated were placed in a glass chamber, and several days later, the rice plants were covered with a cylindrical pipe made of polyvinyl chloride resin and having a diameter of 11 cm and a height of 30 cm, followed by introducing 10 adults (female) of small brown planthopper (*Laodelphax striatellus*) into the cylindrical pipe. 24 Hours after the introduction of the insects, the numbers of the insects killed and the surviving insects were calculated and the rates (%) of the insects killed was periodically evaluated.

These tests were carried out in three-replicates, and an averaged value of the rates (%) of the insects killed as evaluated in the replicate tests was calculated.

As comparative agent was tested such a dust preparation having no sustained release property which was produced in the same manner as in Example 8 but using an untreated bulk powder of NAC in stead of the composite particles of NAC of Example 8.

The results are shown in Table 5.

Test Example 6

Tests for estimating the herbicidal effect and phytotoxicity to plants

Pots each having a size of 1/5000 ares were filled with a soil of paddy rice fields (alluvial soil) and the soil in each of the pots was admixed with 3 g of a chemically compounded fertilizer (with nitrogenous content, phosphatic content and potash content at ratios of 17:17:17) as a base manure. Water was poured into the pots so that the pots were kept under water-flooding conditions.

(1) Test for Phytotoxicity

Young seedlings of an aquatic rice plant (Variety: Nihonbare) at 2-leaf stage were transplanted in the soil at a rate of 3 seedlings per pot. On third day after the transplantation of rice plants, the herbicidal treatment was done by scattering into the pots such a granular preparation having the sustained release property which contained the composite particles of Bifenox as produced similarly to Example 9. The granular preparation was applied at a rate of application of 3 kg per 10 ares. Water was poured into the pots to a depth of the flooding water of 5 cm. The estimation of the phytotoxic effect was made on 21th day after the application of the herbicidal agent by measuring the lengths of such browning regions of the third leaf of rice plants where the regions having brown discoloration could clearly be observed, and then evaluating an average value of the lengths (cm) of the browning regions of leaf.

TABLE 5

| Run No. | Fine particles of hydrophobic substance | Particle diameter (μm) of hydrophobic substance | Angle of contact of hydrophobic substance (degree) | Amount of hydrophobic substance used (weight ratio of hydrophobic substance/pesticidally active ingredient) | Rate (%) of insects killed | | | | Phytotoxicity |
|---|---|---|---|---|---|---|---|---|---|
| | | | | | Directly after treatment | After 3 days | After 7 days | After 14 days | |
| 1 | Titanium oxide MT-100S | 0.015 | 145 | 0.05 | 100 | 100 | 97 | 47 | Not observed |
| 2 | Titanium oxide MT-100S | 0.015 | 145 | 0.25 | 100 | 100 | 97 | 47 | Not observed |
| 3 | Titanium oxide MT-100S | 0.015 | 145 | 0.5 | 100 | 100 | 93 | 50 | Not observed |
| 4 | Titanium oxide MT-100S | 0.015 | 145 | 1.0 | 100 | 100 | 97 | 50 | Not observed |
| 5 | Aerosil R-972 | 0.016 | 155 | 0.25 | 100 | 100 | 97 | 47 | Not observed |
| 6 | Myristic acid | 1.0 | 75 | 0.25 | 100 | 100 | 97 | 53 | Not observed |
| 7 | Calcium stearate | 1.0 | 140 | 0.25 | 100 | 100 | 93 | 47 | Not observed |
| 8 | Comparative agent | — | — | — | 100 | 83 | 40 | 10 | Not observed |
| 9 | Untreated plot | — | — | — | 0 | 0 | 0 | 0 | — |

These tests were carried out in three-replicates, and an averaged value of the lengths (cm) of the browning regions of leaf as evaluated in these replicate tests was calculated.

Furthermore, as comparative agent 1 was tested such a granular preparation having no sustained release property which was formulated in the same manner as in Example 9 but using an untreated powder of Bifenox in place of the composite particles of Bifenox of Example 9.

The results are shown in Table 6.

$$\left(1 - \frac{\text{Dry weight of barnyard glass in treated plot}}{\text{Dry weight of barnyard glass in untreated plot}}\right) \times 100$$

These tests were carried out in three-replicates, and an average value of the rates (%) of kill of weed as evaluated in these replicate tests was calculated.

The results are tabulated in Table 6.

TABLE 6

| Run No. | Fine particles of hydrophobic substance | Particle diameter (μm) of hydrophobic substance | Angle of contact of hydrophobic substance (degree) | Amount of hydrophobic substance used (weight ratio of hydrophobic substance/pesticidally active ingredient) | Ratio of phytotoxicity (length of brown-discolored leave to that in comparative agent-treated plot | Rate (%) of kill of weed | | | | |
|---|---|---|---|---|---|---|---|---|---|---|
| | | | | | | 10 days after seeding | 20 days after seeding | 30 days after seeding | 40 days after seeding | 50 days after seeding |
| 1 | Titanium oxide MT-100T | 0.015 | 140 | 0.05 | 15 | 100 | 100 | 100 | 90 | 78 |
| 2 | Titanium oxide MT-100T | 0.015 | 140 | 0.25 | 14 | 100 | 100 | 100 | 88 | 79 |
| 3 | Titanium oxide MT-100T | 0.015 | 140 | 0.5 | 15 | 100 | 100 | 100 | 88 | 80 |
| 4 | Titanium oxide MT-100T | 0.015 | 140 | 1.0 | 16 | 100 | 100 | 100 | 90 | 77 |
| 5 | Silicone resin | 2.0 | 150 | 0.05 | 18 | 100 | 100 | 100 | 89 | 78 |
| 6 | Silicone resin | 2.0 | 150 | 0.25 | 18 | 100 | 100 | 100 | 90 | 78 |
| 7 | Silicone resin | 2.0 | 150 | 0.5 | 17 | 100 | 100 | 100 | 90 | 80 |
| 8 | Silicone resin | 2.0 | 150 | 1.0 | 15 | 100 | 100 | 100 | 88 | 78 |
| 9 | Stearic acid | 3.0 | 90 | 0.25 | 16 | 100 | 100 | 100 | 88 | 77 |
| 10 | Aluminum stearate | 2.5 | 130 | 0.25 | 18 | 100 | 100 | 100 | 90 | 78 |
| 11 | Comparative agent 1 | — | — | — | 100 (length of brown-discolored leave: 9.0 cm) | 100 | 100 | 100 | 70 | 48 |
| 12 | Comparative agent 2 | — | — | — | 85 | 100 | 100 | 98 | 75 | 52 |
| 13 | Comparative agent 3 | — | — | — | 87 | 100 | 100 | 97 | 73 | 50 |
| 14 | Untreated plot | — | — | — | — | 0 (0.21) | 0 (0.21) | 0 (0.20) | 0 (0.22) | 0 (0.21) |

(2) Test for Herbicidal effect

The herbicidal treatment was conducted by scattering the same granular preparation as described in the above into another pots each having a size of 1/5000 ares which had been kept under the water-flooding conditions. This granular preparation was applied at a rate of application of 3 kg per 10 ares. 10 Days, 20 days, 30 days, 40 days or 50 days after the herbicidal treatment, germinating seeds of barnyard grass were sown at a rate of 20 seeds per pot, followed by pouring water into the pots to a depth of the flooding water of 3 cm. The estimation of the herbicidal effect was made 24 days after each date of sowing the grass seeds by extracting the grass from the soil and measuring of dry weight (g) of the extracted weed. Rate (%) of kill of weed was evaluated according to the following equation:

Rate (%) of kill of weed =

For Table 6:

Note 1): Numerical figures given the brackets in the tests of untreated plot denote dry weights of barnyard grass grown there.

Note 2): Comparative agent 2 (according to an invention of Japanese patent application first publication "Kokai" No. 126402/82). This comparative agent 2 was granular preparation of Bifenox which was obtained by spraying the granules of the comparative agent 1 with a solution containing a polyethylene resin and an polyethylene-acetic acid copolymer resin, followed by drying the so sprayed granules to produce such granules of Bifenox which were each coated with 1% by weight of the mixture of polyethylene resin and polyethylene-acetic acid copolymer resin (at weight ratio of 53:47).

Note 3): Comparative agent 3 (according to an invention of Japanese patent application first publication "Kokai" No. 202801/85). This comparative agent 3 was a granular preparation of Bifenox which was obtained by spraying the granules of the comparative agent 1 with a liquid emulsion containing wax and an acrylic resin, followed by drying the so sprayed granules to produce the granules of Bifenox which were each coated with 2% by weight of the mixture of wax and acrylic resin (at weight ratio of 6:1).

INDUSTRIAL UTILITY OF THE INVENTION

As be described in the above, this invention can provide such a pesticide having the sustained release property which is useful in that the pesticidally active ingredient can be released or dissolved out from said pesticide gradually with the release of the active ingredient lasting or sustaining over a prolonged period of time, and hence in that said pesticide can display a sustaining biological activity of the pesticidally active ingredient.

We claim:

1. A process for the production of a pesticide in the form of composite particles, each composite particle comprising a solid central core of a solid, pesticidally active ingredient and either an outer layer consisting of fine particles of a hydrophobic substance surrounding said core or a continuous coat-film made of said hydrophobic substance, said process comprising
   providing fine particles of the hydrophobic substance having an average particle diameter of not greater than one-fifth of the average diameter of said solid core of the pesticidally active ingredient in such a proportion that the total amount of the hydrophobic substance employed is in a range of 0.05 parts to 1 part by weight per part by weight of said pesticidally active ingredient, and
   adhering said fine particles of the hydrophobic substance to the surfaces of said solid core of the pesticidally active ingredient or partially embedding individual particles of the fine particles of the hydrophobic substance into the surfaces of said solid core of the pesticidally active ingredient such that the hydrophobic substance wholly coats the surfaces of the core of the solid pesticidally active ingredient.

2. A sustained release pesticide comprising solid pesticidal particles, each of said pesticidal particles comprising
   a core of a solid, pesticidally active ingredient, and
   a hydrophobic coating layer comprising fine particles of a hydrophobic substance, each of said fine particles having an average diameter of not greater than one-fifth of the average diameter of said solid core, said hydrophobic coating layer substantially surrounding said core, the total amount of the hydrophobic substance in said coating layer being 0.05 parts to 1 part by weight per part by weight of the amount of pesticidally active ingredient in said core.

3. A sustained release pesticide according to claim 2 wherein said active ingredient is selected from the group consisting of insecticides, fungicides, bactericides, herbicides, and plant growth regulating agents.

4. A sustained release pesticide according to claim 2 wherein said active ingredient is water soluble.

5. A sustained release pesticide according to claim 2 wherein said hydrophobic layer is provided by hydrophobic particles having an average or mean particle diameter of not greater than one fifth of the average or mean particle diameter of said pesticidal particles.

6. A sustained release pesticide according to claim 2 wherein said hydrophobic particles have an average or mean particle diameter of not greater than one tenth of the average or mean particle diameter of said pesticidal particles.

7. A sustained release pesticide according to claim 2 wherein said hydrophobic substance is selected from the group consisting of higher aliphatic acids, metal salts of higher aliphatic acids, titanium dioxide treated with a metal salt of a higher aliphatic acid, hydrophobic white carbon, and hydrophobic synthetic polymers.

8. A sustained release pesticide according to claim 2 wherein said hydrophobic substance is selected from the group consisting of stearic acid, palmitic acid, lauric acid, myristic acid, aluminum stearate, magnesium stearate, calcium stearate, titanium dioxide treated with aluminum laurate, titanium dioxide treated with aluminum stearate, alkylsilylated silica, silicon dioxide treated with dimethyldichlorosilane, a polystyrene, a polyamide and a silicone.

9. A sustained release pesticide according to claim 2 wherein said hydrophobic particles are fixed into the surface of the pesticidal particles.

10. A sustained release pesticide according to claim 2 wherein the pesticidal particles have an average or mean particle diameter in the range of 5 to 500 microns.

11. A sustained release pesticide according to claim 2 wherein said hydrophobic particles have an average or mean particle diameter in the range of 0.01 to 100 microns.

12. A sustained release pesticide according to claim 2 wherein the coated pesticidal particles, including said hydrophobic layer, have an average or mean particle diameter of not more than 50 microns.

13. A process according to claim 1 further comprising subjecting said fine hydrophobic particles adhered to or partially embedded in the surface of said core of each of said composite particles to impacting force or heat of friction or both to integrate and bind the fine hydrophobic particles.

14. A process according to claim 1 wherein each of said fine hydrophobic particles has an average or mean particle diameter not greater than one tenth of the average or mean diameter of said core.

15. A process according to claim 1 wherein said active ingredient is selected from the group consisting of insecticides, fungicides, bactericides, herbicides, and plant growth regulating agents.

16. A process according to claim 1 wherein said active ingredient is water soluble.

17. A process according to claim 1 wherein said hydrophobic substance is selected from the group consisting of higher aliphatic acids, metal salts of higher aliphatic acids, titanium dioxide treated with a metal salt of a higher aliphatic acid, hydrophobic white carbon, and hydrophobic synthetic polymers.

18. A process according to claim 1 wherein the pesticidal particles have an average or mean particle diameter in the range of 5 to 500 microns.

19. A process according to claim 1 wherein said hydrophobic particles have an average or mean particle diameter in the range of 0.01 to 100 microns.

20. A process according to claim 1 wherein the coated pesticidal particles, including said hydrophobic layer, have an average or mean particle diameter of not more than 50 microns.

* * * * *